United States Patent [19]

Finney

[11] 4,364,379

[45] Dec. 21, 1982

[54] PENILE ERECTILE SYSTEM

[76] Inventor: Roy P. Finney, 92 Adriatic Ave., Tampa, Fla. 33606

[21] Appl. No.: 318,583

[22] Filed: Nov. 5, 1981

Related U.S. Application Data

[63] Continuation-in-part of Ser. No. 150,231, May 15, 1980, Pat. No. 4,318,396, and a continuation-in-part of Ser. No. 244,335, Mar. 17, 1981.

[51] Int. Cl.³ .............................................. A61F 5/00
[52] U.S. Cl. .................................................... 128/79
[58] Field of Search .................. 128/79, DIG. 80; 3/1

[56] References Cited

U.S. PATENT DOCUMENTS 4,187,839 2/1980 Nuwayser et al. .................. 128/79
4,224,934 9/1980 Scott et al. ............................ 128/79

Primary Examiner—Stephen C. Pellegrino
Attorney, Agent, or Firm—Quarles & Brady

[57] ABSTRACT

A penile erectile system which is adapted to be surgically implanted in man for the treatment of erectile impotence includes an elongated penile implant adapted to be implanted in the corpus cavernosum of a penis, said member including a stem at one end, a tip at the other end, first and second chambers axially positioned between the stem and tip, said first chamber having a resilient non-collapsible wall and the second chamber having a flexible non-distensible wall. Both of the chambers are normally substantially filled with fluid and are connected by a passage closed by a valve which normally permits fluid to only flow from the first to the second chamber but which can serve as a relief valve when the pressure in the second chamber exceeds a predetermined pressure.

4 Claims, 4 Drawing Figures

PENILE ERECTILE SYSTEM

RELATED APPLICATION

The present application is a continuation in part of my earlier copending patent applications Ser. No. 150,231 filed May 15, 1980, now U.S. Pat. No. 4,318,396, and Ser. No. 244,335 filed Mar. 17, 1981.

FIELD OF THE INVENTION

The present invention relates to a novel penile erectile system. More particularly, it relates to a pressurizable implantable penile erectile system which is useful in the treatment of erectile impotence.

DESCRIPTION OF THE PRIOR ART

Some cases of erectile impotence do not respond to conventional therapy and the surgical implanting of a penile erectile system may be the only practical means of remedying the impotency.

Several different types of penile erectile systems have been employed in the past. One type of penile erectile system which is currently available is an inflatable system. The inflatable system includes two fairly long inflatable and distensible tubes that are surgically implanted in the corpus cavernosum of the penis. Each of the two tubes is connected by tubing to a relatively large pressure bulb of inflating fluid which is implanted elsewhere in the body, necessitating additional abdominal or scrotal surgery. The systems of U.S. Pat. Nos. 3,954,102 and 4,909,711 are representative of inflatable penile erectile systems.

Another type of penile erectile system in use comprises a pair of rods of suitable stiffness which are surgically implanted into the corpus cavernosum of the penis. A significant advantage of this system is that the amount of surgery involved is minimal, as there is no pressure bulb to implant. A disadvantage of this system is the permanent stiffness of the rods can be a source of physical pain and embarrassment to the patient. Representative penile erectile systems employing rod implants are the systems disclosed in U.S. Pat. Nos. 3,893,476 and 4,066,037.

SUMMARY OF THE INVENTION

It is the general object of the present invention to disclose a novel pressurizable implantable penile erectile system.

It is a further object to disclose a pressurizable implantable penile erectile system that can be implanted completely in the penis making abdominal or scrotal surgery unnecessary.

In its simplest form the entire penile erectile system of the present invention is contained in a single penile implant, however, two implants preferably are used.

The preferred implant of the penile erectile system of the present invention has a relatively short, proximal stem, a distal tip, first and second chambers axially positioned between the stem and tip, the said first chamber having a resilient, non-collapsible wall and the second chamber having a flexible non-distensible wall. Both chambers substantially are filled with hydraulic fluid and connected by a passage so that hydraulic fluid can be transferred from one chamber to the other chamber, and there is valve means for controlling the flow of fluid between the chambers and the pressure in the second chamber.

In the preferred embodiment, the first chamber has a relatively thick resilient wall which resists collapsing and will support the penis in an erectile position and the second chamber adjacent the tip has a flexible, non-distensible wall. The second chamber is normally substantially filled with fluid but unpressurized allowing the penis to assume a flaccid position. However, it can be pressurized by transferring fluid thereto from the first chamber. When pressurized the second chamber is rigid and causes the penis to assume an erectile position. The preferred valve means operates as a check valve in one direction and a relief valve in the opposite direction.

Since the entire system is contained in the implant, it can be implanted as easily as the prior art penile rod implants. The only surgery required is that to place and position the implants in the corpus cavernosum of the penis.

When the implants are in place and the second chamber is unpressurized the penis normally assumes a flaccid state. However, when the hydraulic fluid is transferred under pressure from the first chamber into the second chamber, the second chamber becomes rigid causing the penis to assume an erectile position.

The penile erectile system of the present invention, in addition to being compact and thus minimizing the amount of surgery required, has a minimum number of fluid connections, thus reducing risk of leakage.

The foregoing and other objects and advantages will become apparent from the description which follows:

DESCRIPTION OF THE PREFERRED EMBODIMENTS

Figure 1:
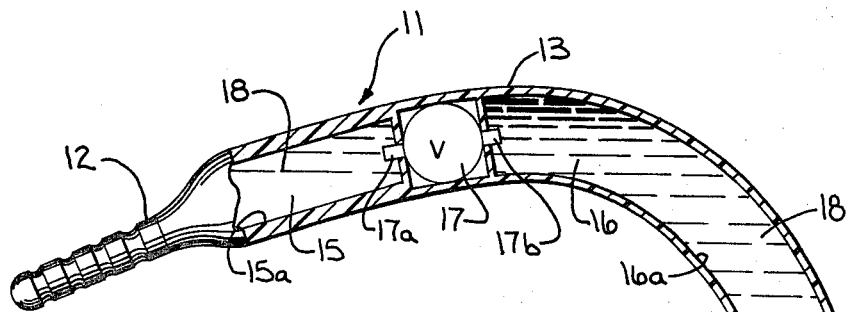
FIG. 1 is a side view, partly in section, of a preferred embodiment of an implanted penile erectile system of the present invention in a non-pressurized condition.

The preferred embodiment of the penile erectile system as seen in the drawings, comprises a pair of elongated implants 11, only one of which is shown. The two implants are identical; therefore, only one will be described in detail.

Figure 2:
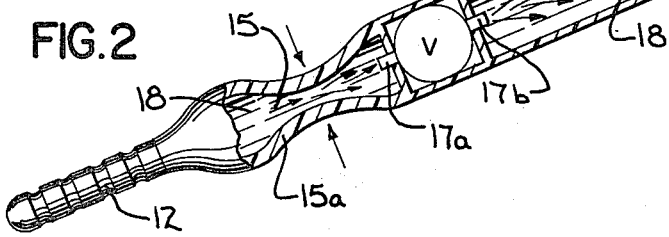
FIG. 2 is a side view similar to FIG. 1, except that the second chamber is being pressurized.
Figure 3:
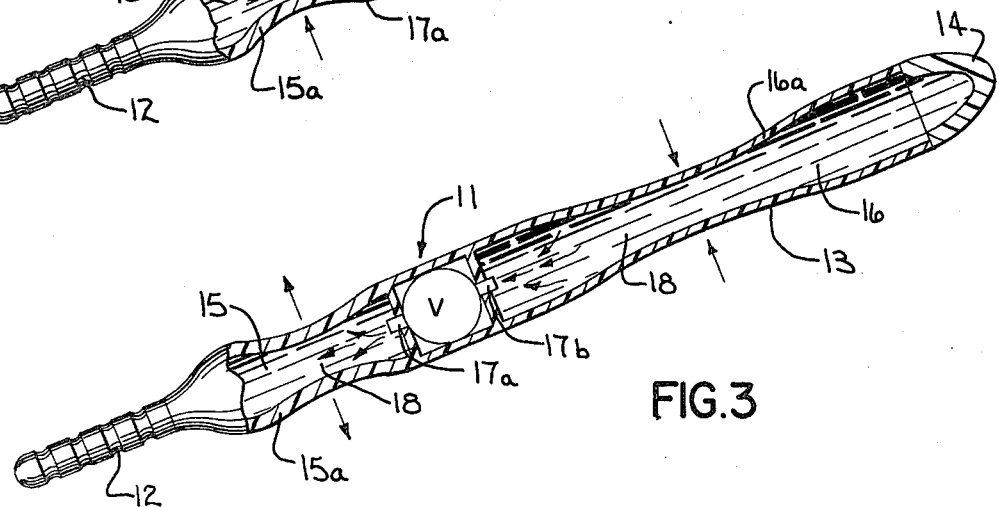
FIG. 3 is a side view similar to FIG. 1 except that the second chamber is being depressurized.

As seen in FIGS. 1 to 3, the implant 11 has a short, proximal stem 12 of relatively stiff material which is intended to be implanted in the root end of a corpus cavernosum to support and anchor the implant, an intermediate cylindrical portion 13, and a conical distal tip 14. The tubular portion 13 and the tip 14, which are soft and flexible, are intended to be implanted in the portion of the corpus cavernosum in the pendulous penis. When implanted, each of the two implants is positioned in a separate corpus cavernosum of the penis.

Figure 4:
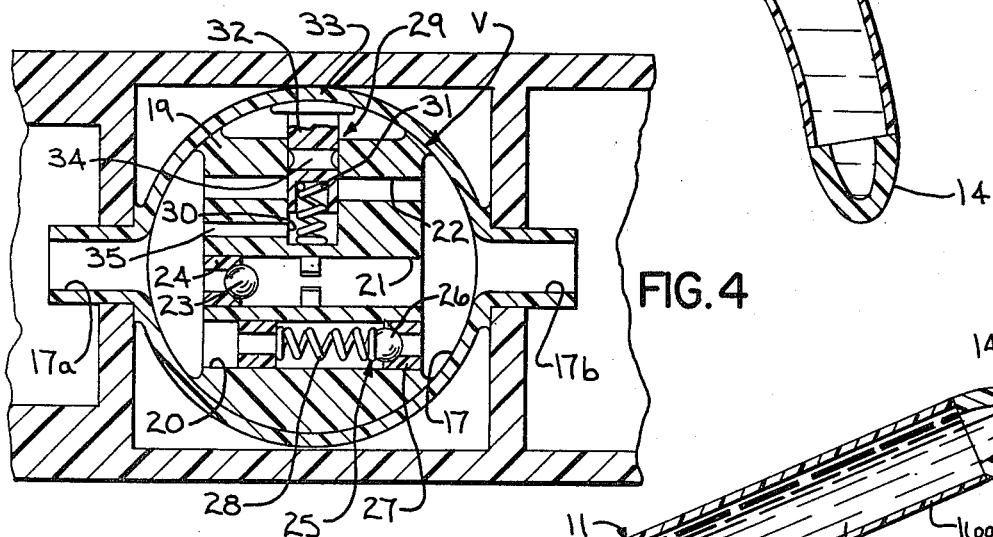
FIG. 4 is an enlarged sectional view of the valve.

Still referring to FIGS. 1 to 3, it can be seen that the intermediate cylindrical portion 13 of the implant 11 includes a pair of axially aligned chambers 15 and 16, respectively, which are connected by a passage 17 having an inlet 17a and an outlet 17b. A valve means seen in detail in FIG. 4 is located between the inlet 17a and outlet 17b of the passage 17. The preferred valve means is that disclosed in U.S. Pat. No. 4,167,952, which is incorporated by reference herein.

Returning to FIG. 1, it can be seen that even in a non-pressurized state the chambers 15 and 16 are both substantially filled with a non-compressible biocompatible hydraulic fluid 18 such as saline or a free flowing silicone gel. The first chamber 15 which has a relatively thick resilient wall 15a which resists collapsing and the second chamber 16 has a flexible wall 16a which permits the penis to assume the substantially normal, flaccid position seen in FIG. 1 when the chamber is not pressurized. When chamber 16 is completely filled and pressurized, wall 16a which is non-distensible causes the chamber 16 to become rigid and the penis to assume an erectile position as seen in FIG. 2.

As seen in FIG. 2, the chamber 16 is pressurized by forcibly squeezing the wall 15a of the chamber 15 to force hydraulic fluid 18 out of the first chamber 15 through the inlet 17a of the passage 17 and the valve means and out the outlet 17b thus filling the non-distensible chamber 16 with fluid 18 under pressure. When the chamber 16 is sufficiently pressurized and rigid, the squeezing of chamber 15 is stopped whereby the valve means closes and prevents fluid 18 from returning to chamber 15. The second chamber 16 remains completely filled, pressurized and rigid and the chamber 15 partially emptied but not collapsed, as seen in FIG. 2, until the valve means is opened to permit fluid 19 to flow back to chamber 15. The chamber 16 can be partially emptied most conveniently by squeezing the chamber 16, as seen in FIG. 3, thus increasing the pressure therein above the predetermined pressure at which the valve means 18 operates as a relief valve and opens to permit fluid to flow back to chamber 15. The squeezing of chamber 16 continues until the chamber 16 is sufficiently emptied so that the penis assumes its normal flaccid position.

A variety of valve means other than that disclosed in U.S. Pat. No. 4,167,952, can be used. In any case, the valve means should be of the type which opens when chamber 15 is squeezed, automatically closes when the squeezing stops and automatically opens to permit fluid to flow from chamber 16 to chamber 15 when a predetermined pressure is exceeded in chamber 16.

Another suitable valve means is shown in FIG. 4. As seen therein, the valve includes a valve body 19 having passages 20, 21 and 22 extending therethrough. A one way valve mechanism is mounted in passage 21 which comprises a ball 23 and a seat 24 for the ball, when chamber 15 is squeezed the ball 23 is off its seat 24 permitting fluid to be pumped from chamber 15 into chamber 16. When pressure in chamber 16 exceeds that in chamber 15 the ball 23 is on its seat 24 as seen in FIG. 4 preventing fluid from flowing in the opposite direction.

Mounted in passage 20 is a relief valve 25 which comprises a ball 26, a seat 27 and a calibrated spring 28. The relief valve 25 is normally closed as seen in FIG. 4, but opens when the pressure in chamber 16 exceeds a predetermined level above its operating pressure. At the time, the pressure sensed by the ball 26 exceeds the force of the spring 28 and the ball 26 is moved off its seat 27. As soon as the pressure in chamber 16 falls below the predetermined level the force of the spring 28 moves the ball 26 onto its seat 27 closing the passage 20 to flow.

The third passage 22 is normally closed by an upset valve 29 and it is used to rapidly depressurize chamber 16. The upset valve 29 includes a bore 30 in the valve body 19. Positioned in the bore 30 is spring 31 and a piston 32 having an enlarged head 33. The piston 32 has a radial opening 34 extending therethrough which can be aligned with passage 22 by moving the piston 32 downward in the bore 30 thereby compressing the spring 31. When the piston 32 is moved downward, fluid in the bore 30 flows via the vent 35 to the inlet 17a. Once the opening 34 is aligned with the passage 22 fluid 18 leaves chamber 16, the pressure between chambers 15 and 16 is equalized and the implant 11 assumes the position seen in FIG. 1. Upon release of the downward pressure on the piston head 33 the spring 31 returns the piston 32 to its original position closing the passage 22.

The relief valve 25 serves both as another means of depressurizing the chamber 16 and a means of protecting the implant from pressure damage. For example, if the operating or working pressure for chamber 16 is 300 mm. Hg. and the chamber 16 has a bursting pressure of 450 mm. Hg., a relief valve which opens at 400 mm. of Hg. will protect the implant from a bursting pressure which could result from the implant being accidentally struck or bent.

The term "substantially filled" as used herein to describe the fluid content of the chambers 15 and 16 means that chambers contain about 60% to about 95% or more of their capacity of a non-compressible fluid such as water, saline or a free flowing gel. The actual content of fluid can vary; however, the distal portion of the implant even "substantially filled" is still sufficiently flexible so that the penis will assume a normal flaccid position.

All the parts and components of the implant are preferably made of a biocompatible material or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The second chamber 16 must provide when pressurized rigidity sufficient to maintain the penis in an erectile position. Therefore, it must be of sufficient volume and size to perform this function either alone or in combination with another implant. Preferably the chamber 16 has a volume of about 12 cc. In contrast, the first chamber 15 serves as a reservoir of pressurizing fluid for the chamber 16 and is sized accordingly containing only about 6 cc. of fluid. The exact dimensions of the chambers are not critical as long as they are adequate to provide their desired functions. The diameters of the chambers 15 and 16 can vary but are normally sized so that when they are substantially filled with fluid they will fill the corpus cavernosum in which they are implanted.

The wall 16a of the second chamber 16 is non-distensible under conditions of use and preferably is made of a dacron mesh or fabric covered with silicone elastomer so that it will expand only to a limited extent or will not stretch. As a result, chamber 16 can be filled and pressurized by the transfer of relatively small amounts of fluid.

The resilient wall 15a of chamber 15 may be made of reinforced or unreinforced silicone rubber. The wall 15a although resilient, must not collapse even when partially emptied of fluid as it must support the implant 11 during an erection.

The proximal stems of the implants preferably have a Shore A hardness of about 70, the distal tips a Shore A hardness of about 20, and each of the materials has sufficient tensile strength for its intended use. In the preferred embodiments of the drawings, the tips are tapered and made of or filled with a self-sealing silicone elastomer to allow fluid to be added to or removed from the chambers with a hollow needle and syringe (not shown).

The preferred method of implantation of the erectile system of the present invention is through incisions made in the penis. After an appropriate incision, the corpus cavernosum is dilated distally and proximally to accept the implant. The appropriate anatomical measurements are made to insure that the proximal stem of the implant or implants will be positioned at the base of the penis below the pelvic bone. An implant or implants having an appropriately sized intermediate section and distal tip is inserted into the corpus cavernosum of the penis. The distal tip is positioned in the glans end of the corpus cavernosum. The proximal stem of the implant then is anchored in the root end of the corpus cavernosum.

The identical procedure is performed on the other side of the penis to complete the surgical procedure. The proximal stems of the two implants preferably will diverge laterally to accommodate the anatomy and provide lateral stability to the penis. The incisions are then closed.

It is to be understood that the foregoing description has been for purposes of illustration and that a number of modifications and changes may be made without departing from the spirit and scope of the present invention. For example, although the implants described have solid stems for anchoring the implants, the stems could be hollow, if desired.

The invention is not to be limited by any of the specific embodiments described but only by the claims which follow:

I claim:

1. A penile erectile system comprising an elongated penile implant having a stem at one end, a tip at the other end, a first and second chamber axially positioned between the stem and tip, said first chamber having a resilient, non-collapsible wall and the second chamber having a flexible, non-distensible wall, both of said chambers being substantially filled with fluid, a passage providing communication between the first and second chambers and valve means in said passage for controlling the flow of fluid between the chambers, said valve means serving as a check valve which normally permits flow only from said first to second chamber and a relief valve which permits flow from the second chamber to the first chamber when the pressure in the second chamber exceeds a predetermined pressure.

2. The implant of claim 1 in which the first chamber has a relatively thick wall.

3. The implant of claim 1 which includes a self-sealing tip.

4. The implant of claim 1 in which the valve means includes an upset valve for quickly equalizing pressure between the first and second chambers.

* * * * *